United States Patent [19]

Aretz et al.

[11] Patent Number: 5,766,881
[45] Date of Patent: Jun. 16, 1998

[54] INDUCTION-FREE PROCESS FOR THE RECOMBINANT PREPARATION OF GLUTARYLAMIDASE

[75] Inventors: Werner Aretz, Künigstein; Ulrich Holst, Diez; Klaus Peter Koller, Bad Soden, all of Germany

[73] Assignee: Hoechst Aktiengesellschaft, Frankfurt am Main, Germany

[21] Appl. No.: 544,087

[22] Filed: Oct. 17, 1995

[30] Foreign Application Priority Data

Oct. 19, 1994 [DE] Germany .......................... 44 37 420.8

[51] Int. Cl.$^6$ .............. C12P 21/02; C07H 21/04; C12N 15/56; C12N 15/70
[52] U.S. Cl. ............... 435/69.1; 435/172.3; 435/320.1; 536/24.1
[58] Field of Search ..................... 435/69.1, 172.3, 435/320.1, 195, 47; 536/24.1; 935/41, 72

[56] References Cited

U.S. PATENT DOCUMENTS

| | | | |
|---|---|---|---|
| 3,766,010 | 10/1973 | Ikeda et al. | 195/30 |
| 4,981,789 | 1/1991 | Lein | 435/51 |
| 5,229,274 | 7/1993 | Crawford et al | 435/69.1 |
| 5,256,568 | 10/1993 | Panayotatos | 435/252.33 |
| 5,320,948 | 6/1994 | Iwami et al. | 435/47 |
| 5,559,005 | 9/1996 | Conder et al. | 435/47 |

FOREIGN PATENT DOCUMENTS

| | | |
|---|---|---|
| 0 469 919 A2 | 2/1992 | European Pat. Off. |
| 0 504 798 A1 | 9/1992 | European Pat. Off. |

OTHER PUBLICATIONS

Baldwin et al., "High level expression in *Escherichia coli* of a fungal gene under the control of strong promoters", FEMS Microbiol. Letts. 68: 45–52, 1990.

Varma et al., "Biochemical production capabilities of *Escherichia coli*", Biotech. Bioengineer. 42: 59–73, 1993.

Isogai et al., "Construction of a 7–Aminocephalosphoranic Acid (7ACA) Biosynthetic Operon and Direct Production of 7ACA in Acremonium Chryosgenum," Bio/Technology, 9:188–191, Feb. 1991.

European Search Report.

Matsuda et al., Journal of Bacteriology, 163:1222–1228 (1985).

Shibuya et al., Agricultural and Biological Chemistry, 45:1561–1567 (1981).

Glover, Gene Cloning, pp. 110–127 (1984).

Skatrud, Biotechnology, 7:477–485 (1989).

Schumacher et al., Nuc. Acids Res., 14:5713–5727 (1986).

Oh et al., Gene, 56:87–97 (1987).

European Search Report Dated Jul. 13, 1992.

Chang et al., "Construction and Characterization of Amplifiable Multicopy DNA Cloning Vehicles Derived from the P15A Cryptic Miniplasmid," J. Bacteriology 134(3):1141–56 (1978).

Amann et al., "Tightly Regulated tac Promoter Vectors Useful For the Expression of Unfused and Fused Proteins in *Escherichia coli*," Gene 69:301–15 (1988).

Close et al., "Construction and Characterization of the Chloramphenicol–Resistance Gene Cartridge: A New Approach to the Transcriptional Mapping of Extrachromosomal Elements," Gene 20:305–16 (1982).

*Primary Examiner*—Nancy Degen
*Attorney, Agent, or Firm*—Finnegan, Henderson, Farabow, Garrett & Dunner, L.L.P.

[57] ABSTRACT

Improved, induction-free process for the recombinant preparation of glutarylamidase. The invention relates to a recombinant process for preparing glutarylamidase (GA), wherein the GA gene is expressed constitutively from an expression vector. In certain embodiments, the promoter for constitutively expressing the GA gene is a trc promoter or a trc-equivalent promoter which does not have any repressor or has a non-functional repressor.

9 Claims, 7 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CATGCTGAGA GTTCTGCACC GGGCGGCGTC CGCGACTCTC AAGACGTGGC CCGCCGCAGG      60

CGGAAC                                                                 66
```

( 2 ) INFORMATION FOR SEQ ID NO:2:

( i ) SEQUENCE CHARACTERISTICS:
        ( A ) LENGTH: 240 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

```
TGCCAGGCAT CAAATTAAGC AGAAGGCCAT CCTGACGGAT GGCCTTTTTG CGTTTCTACA      60

AACTCTTTTT GTTTATTTTT CTAAATACAT TCAAATATGT ATCCGCTCAT GAGACAATAA     120

CCCTGATAAA TGCTTCAATA ATGATCCGAG ATTTTCAGGA GCTAAGGAAG CTAAAATGGA     180

GAAAAAAATC ACTGGATATA CCACCGTTGA TATATCCCAA TGGCATCGTA AAGAACATTT     240
```

( 2 ) INFORMATION FOR SEQ ID NO:3:

( i ) SEQUENCE CHARACTERISTICS:
        ( A ) LENGTH: 58 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Cys Gln Ala Ser Asn Ala Glu Gly His Pro Asp Gly Trp Pro Phe Cys
  1               5                  10                  15

Val Ser Thr Ala Arg His Gln Ile Lys Gln Lys Ala Ile Leu Thr Asp
                 20                  25                  30

Gly Leu Phe Ala Phe Leu Gln Pro Gly Ile Lys Leu Ser Arg Arg Pro
             35                  40                  45

Ser Arg Met Ala Phe Leu Arg Phe Tyr Lys
         50                  55
```

INDUCTION-FREE PROCESS FOR THE RECOMBINANT PREPARATION OF GLUTARYLAMIDASE

DESCRIPTION

Improved, induction-free process for the recombinant preparation of glutarylamidase In the enzymic preparation of 7-aminocephalosporanic acid (7-ACA) from cephalosporin C, the enzyme glutarylamidase (GA) is required unconditionally for eliminating the glutaryl side chain. In this context, European Patent Application EP-A-0 469 919 describes a recombinant process for preparing GA in which the expression of GA is induced by way of the tac promoter. Only low yields of GA are obtained. EP-A-0 504 798 described a process by which high yields of GA (from 7,000 to 10,000 U/l of culture medium) are successfully achieved using transformed E. coli bacteria and a specially adapted fermentation method. This method makes the overall process economical. 1 Unit of enzyme activity is defined as the amount of enzyme, which liberates 1 μmol 7-ACA per minute at a temperature of 37° C. and a pH of 7.

The present inventors have found, surprisingly, that a further improvement in the yield can be obtained, so that it is approximately two to two and a half times as great. This improvement is achieved by constitutively expressing the GA gene, i.e., continuous expression of the GA gene, for example, by inactivating the lac $I^q$ repressor, which is likewise plasmid-encoded, and/or by reducing the expression of the intracellularly active selection marker, for example, the plasmid-encoded selection marker chloramphenicol acetyltransferase (CAT). Said reduced expression of the selection marker, which can also be termed "weak expression" is explained on page 4, 1st and 2nd paragraph of this specification and is further described in the examples, i.e. example 1.

The present invention therefore relates to a process for preparing GA in bacteria, where the GA gene is expressed constitutively from an expression vector. In certain preferred embodiments, the promoter for constitutively expressing the GA gene is a trc promoter or a trc-equivalent promoter which does not have any repressor or has a non-functional repressor.

According to certain preferred embodiments, it is particularly advantageous if the expression vector for constitutively expressing the GA gene additionally contains a selection gene which encodes a protein which remains in bacteria and is not periplasmic, for example chloramphenicol acetyltransferase (CAT), especially if this selection protein is only expressed weakly.

The inactivation of the lac $I^q$ repressor gene results in strong, continuous expression and secretion of the GA enzyme without the growth of the E. coli strain being impaired or cell lysis occurring as a result of overexpression.

It is, therefore, also possible to consider using other constitutive promoters, i.e. which are not regulated by induction, for expressing the GA. In contrast to the T 363 E. coli clones, corresponding recombinant clones utilizing constitutive promoters no longer need to be induced with IPTG, leading to further simplification of the process.

EP-A-0 504 798 describes the construction of the expression plasmid T 363 and its transformation into E. coli K 12 W 3110. This patent also describes the plasmid pCM 145, which has already been deposited in the Deutsche Sammlung für Mikroorganismen [German collection of micoroorganisms] under the deposition no. DSM 6409 in accordance with the Budapest Treaty and, inter alia, contains the origin of replication of the known low-copy plasmid pACYC 184 (A. C. Y. Chang and S. N. Cohen, J. Bact. 134 (1978) 1141 to 1156) and the complete gene for a Pseudomonas GA. FIG. 2 shows a restriction map of plasmid pCM 145, together with enumeration of the restriction enzyme cleavage sites which are important for cloning.

One can clone the GA gene into the vector pTrc 99 A (E. Amann et al., Gene 69 (1988) 301 to 315) using a synthetic linker (SEQ ID NO:1):

(NcoI) (StyI)
C ATG CTG AGA GTT CTG CAC CGG GCG GCG TCC GC
  GAC TCT CAA GAC GTG GCC CGC CGC AGG CGG AAC

An 0.57 kb BamHl(4)-StyI(2) fragment is isolated from plasmid pCM 145 following digestion with the enzymes StyI and BamHl (in the published DNA sequence, the StyI cleavage site is located in the region of amino acids 11 to 13). This fragment, and the above-mentioned linker, are ligated into the plasmid pTrc 99 A, which has been cut with NcoI and BamHl, to give the plasmid T 297 with the loss of the NcoI cleavage site.

In addition, a 1.5 kb SalI fragment (SalI(6)-SalI(9)) and an 0.34 kb BamHI-SalI fragment are isolated from plasmid pCM 145 and ligated into the vector pUC 18, which was opened with SalI and BamHl. This gives the plasmid T 306, which was examined for correct orientation of the SalI(6–9) fragment. A 2.1 kb fragment (which encompasses the fragment from the BamHl (4) site to the SalI(9) site) is isolated from plasmid T 306 using the enzymes BamHl and HindIII. This fragment was ligated into vector T 297, which had been opened with the enzymes BamHl and HindIII, to give the plasmid T 307 (FIG. 3). After a fermentation of 2 days at 28° C., the E. coli population which is transformed with this plasmid produces up to 260 U/l GA. If the fermentation conditions are changed, this yield can be increased to greater than 780 U/l.

Induction of the system with IPTG at 37° C. is lethal for the transformed E. coli strain, evidently as the result of using the high copy number vector T 307 and simultaneous coexpression of the β-lactamase, which is likewise secreted. The induction is therefore carried out at temperatures which are less than about 30° C.

Plasmid T 307 possesses a β-lactamase gene whose gene product, the enzyme β-lactamase, is used for selecting recombinant clones. Like GA, β-lactamase is a secreted, periplasmically located enzyme. It was possible to achieve a further improvement in yield by replacing the β-lactamase structural gene, in particular the signal peptide region, with the chloramphenicol acetyltransferase gene. Chloramphenicol acetyltransferase is located exclusively in the cytoplasm of the cell and is not, therefore, secreted into the periplasmic space. The constructions which were carried out gave rise to the plasmid T 363 (FIG. 4), which is also described in European Application EP-A-0 504 798.

It is particularly advantageous for recovering the GA if expression of the CAT gene product, for example, is reduced. When expressed in vector T 363 by way of its natural promoter, chloramphenicol acetyltransferase is a protein which occurs in vast quantity in the disruption material. Reducing its expression results in a marked improvement in the ratio of E. coli protein to GA in favor of the GA, thereby making it possible to increase the separation column loading and to purify more GA per unit of time. The corresponding vector constructs T 396, T 406 and T 415, in which CAT expression is reduced, are depicted in FIGS. 5 to 7.

The invention also relates, therefore, to a process in which the selection protein employed is preferably only expressed weakly.

It was furthermore found that certain preferred embodiments of the fermentation method, which are elucidated below, surprisingly lead to an extension of the growth phase of the bacteria, preferably E. coli, without any accumulation of acetate. This leads additionally to an increase in the biomass yields.

It was possible to improve the fermentation method by increasing the rate at which the carbon source is fed in during the main culture, preferably during the logarithmic phase of growth. Examples of carbon sources which typically can be used are sugars, alcohols or organic acids, preferably glucose or glycerol, in particular glycerol. Examples of complex nitrogen sources which typically can be used are yeast extract, meat peptones, casein peptones and other complex nitrogen sources which are known to the person skilled in the art. The concentration of the complex nitrogen sources in the main culture medium typically is approximately 10–50 g/l, preferably 20–40 g/l, in particular approximately 40 g/l.

The term "main culture" is used in the meaning known to any person skilled in the art: a main culture is a high volume culture which is inoculated with a certain amount of the low volume preculture.

The following examples provide a more detailed description of the expression vector constructions and the fermentative measures according to certain preferred embodiments that achieve the increased yields. The enzymes used for the cloning were obtained from New England Biolabs or Gibco/BRL and used in accordance with the manufacturers' instructions. All values regarding the size of the plasmids (bp) are approximate.

EXAMPLE 1

Reducing expression of the CAT gene (plasmid T 396)

Figure 3:
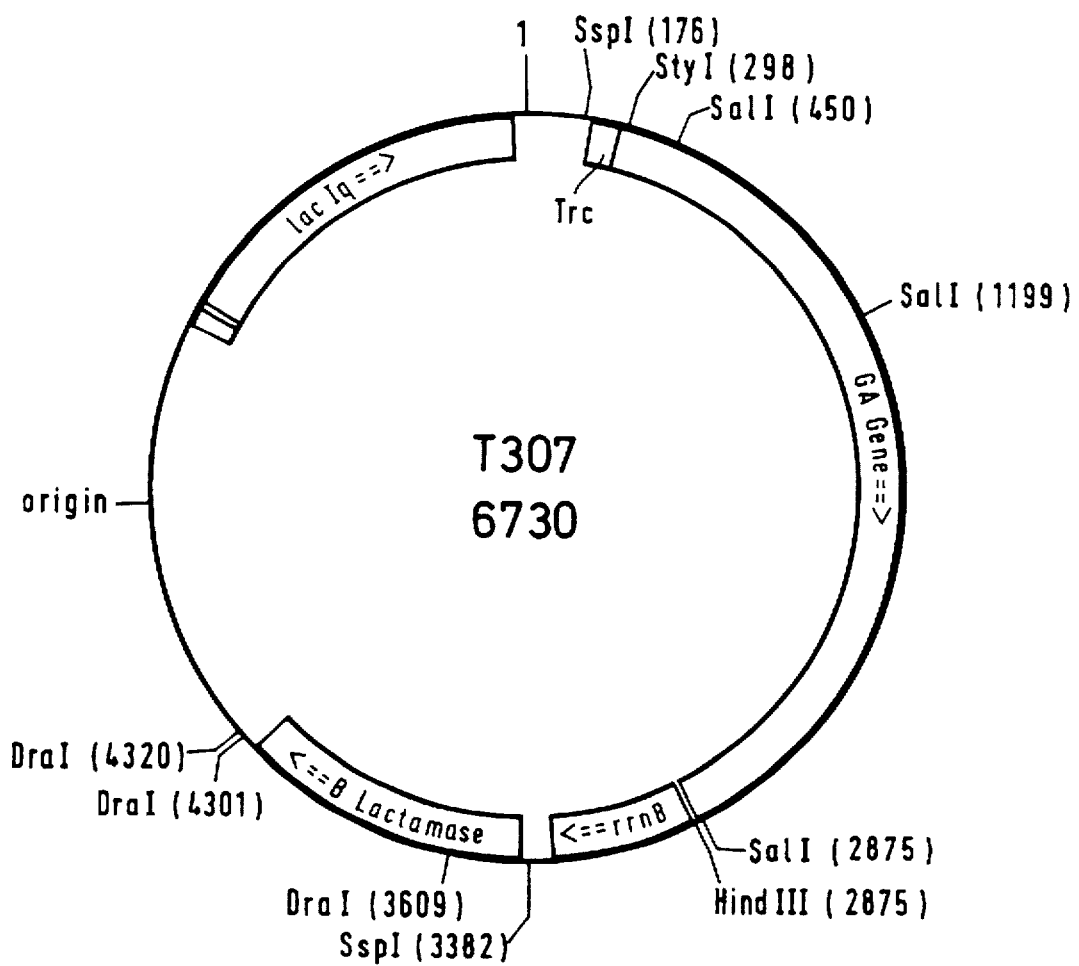

In order to reduce the CAT expression, a promoterless CAT gene was cloned behind the β-lactamase promoter. For this purpose, isolated T 307 plasmid DNA (FIG. 3) was completely digested with the restriction enzymes SspI and DraI and the resulting fragments were fractionated on an 0.6% agarose gel. The approximately 3200 bp SspI fragment containing the GA gene and the approximately 2600 bp SspI-DraI fragment containing the lac I$^q$ gene and the origin of replication of the vector were then isolated by electroelution.

The promoterless CAT gene was obtained from the plasmid pCM 4 (T. Close and R. Rodriguez, Gene 20 (1982), 305 to 316) as follows. Isolated pCM 4 plasmid DNA was completely cut with the restriction enzyme BamHI and the protruding ends were filled in with DNA polymerase I in the presence of ATP, TTP, CTP and GTP, thereby giving rise to blunt-ended fragments. Following agarose gel electrophoresis of the digestion mixture in 1.2% agarose, the fragment of approximately 780 bp in size containing the CAT gene was isolated by electroelution.

Figure 1:
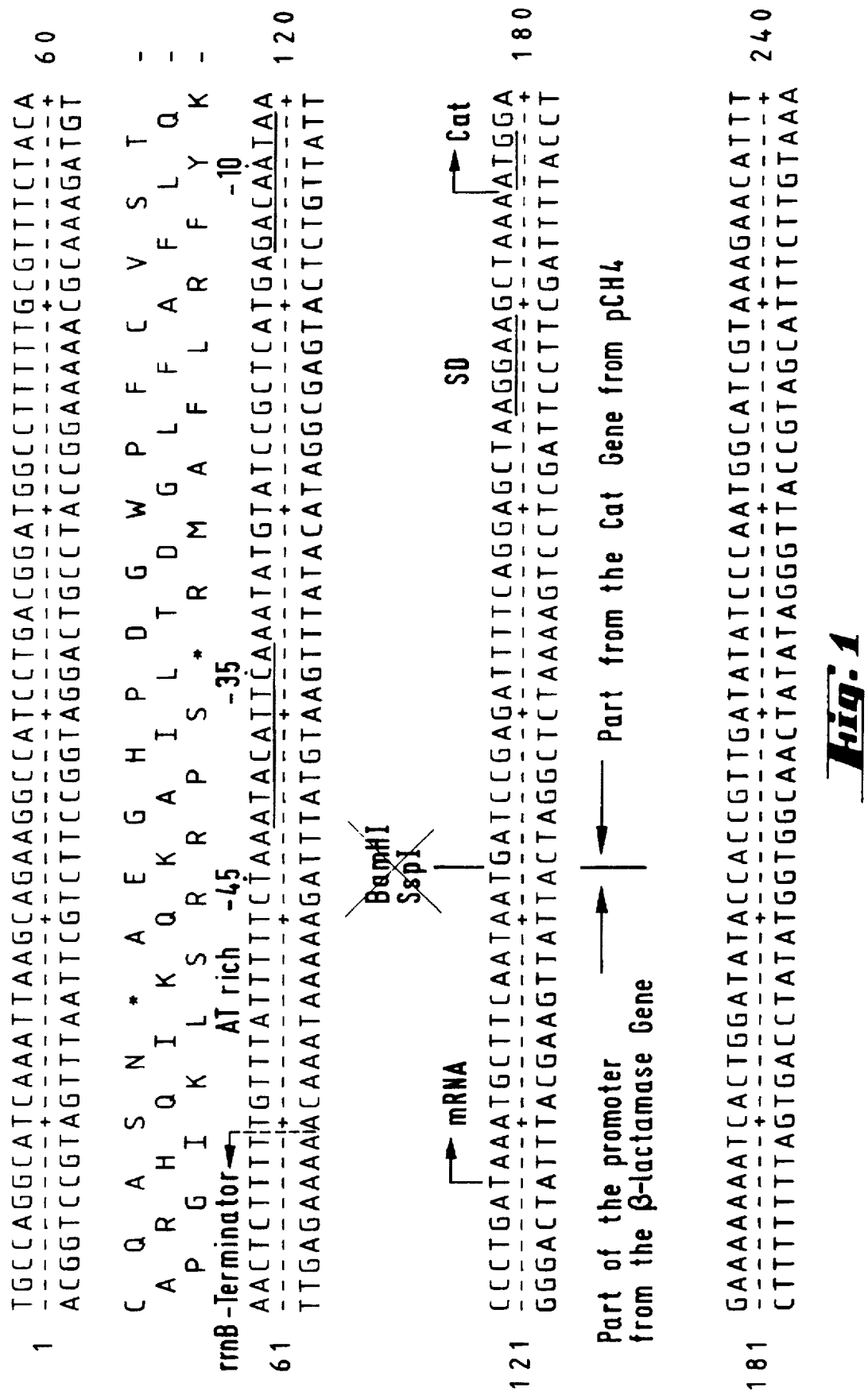
FIG. 1: The CAT gene promoter junction for decreasing the rate at which the CAT gene is expressed (SEQ ID NO:2) and SEQ ID NO:3.
Figure 2:
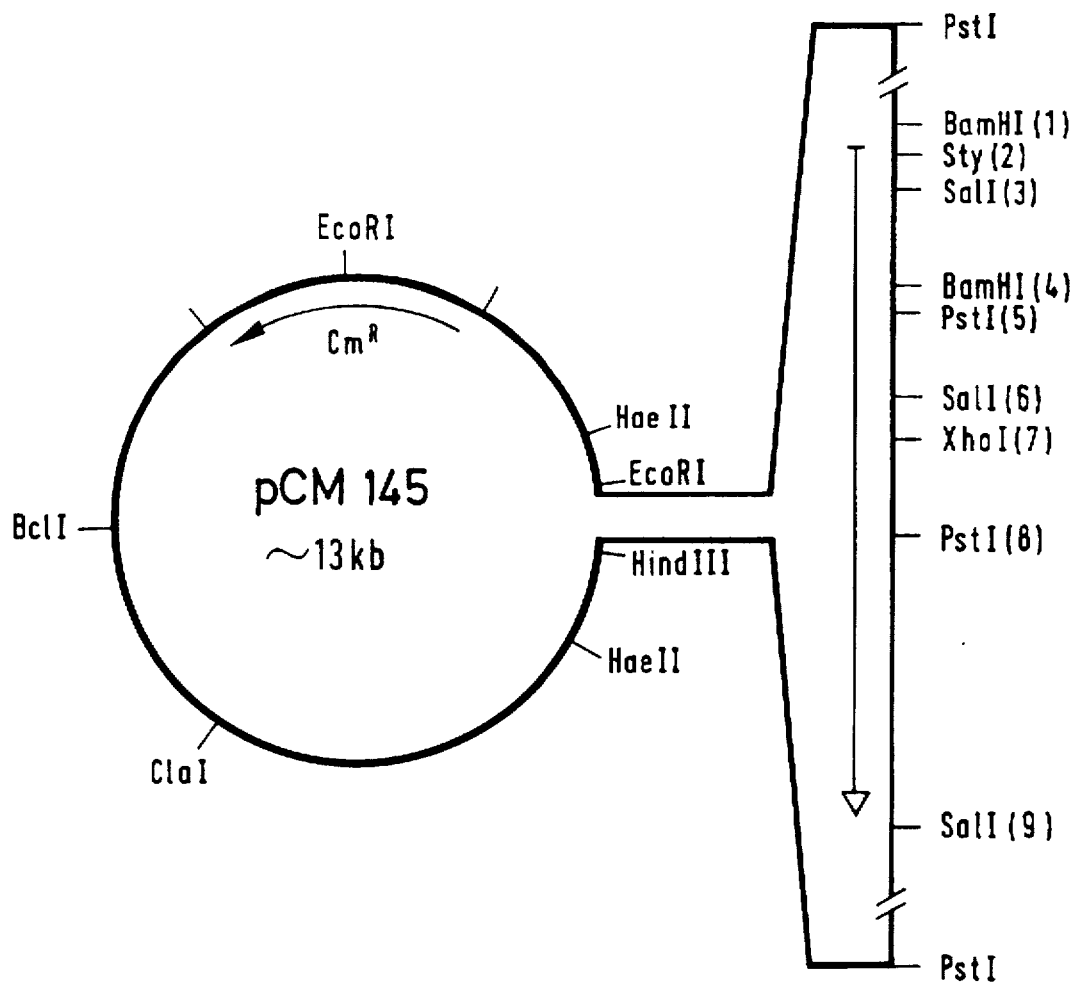
FIGS. 2–7: Expression vectors pCM 145, T 307, T 363, T 396, T 406 and T 415.

This fragment and the two, 3200 bp and 2600 bp, fragments from T 307 were then ligated together in a ligation mixture using DNA ligase. The ligation mixture was transformed into E. coli W 3110 M and those recombinant clones were isolated which only grew optimally in the presence of reduced concentrations of chloramphenicol (12.5 μg/ml) and exhibited glutarylamidase formation. Isolated, chloramphenicol-resistant, clones harbored plasmids containing the three fragments, with the 2600 bp fragment being present in 2 orientations. The best product yield was obtained using plasmid T 396. The lower level of resistance as compared with that of T 363 (25 μg/ml) is due to the fact that the CAT gene is not optimally aligned with the β-lactamase promoter. The junction of the CAT gene with the residue of the β-lactamase promoter sequence is depicted in FIG. 1 (SEQ ID NO:2 and SEQ ID NO:3).

Figure 4:
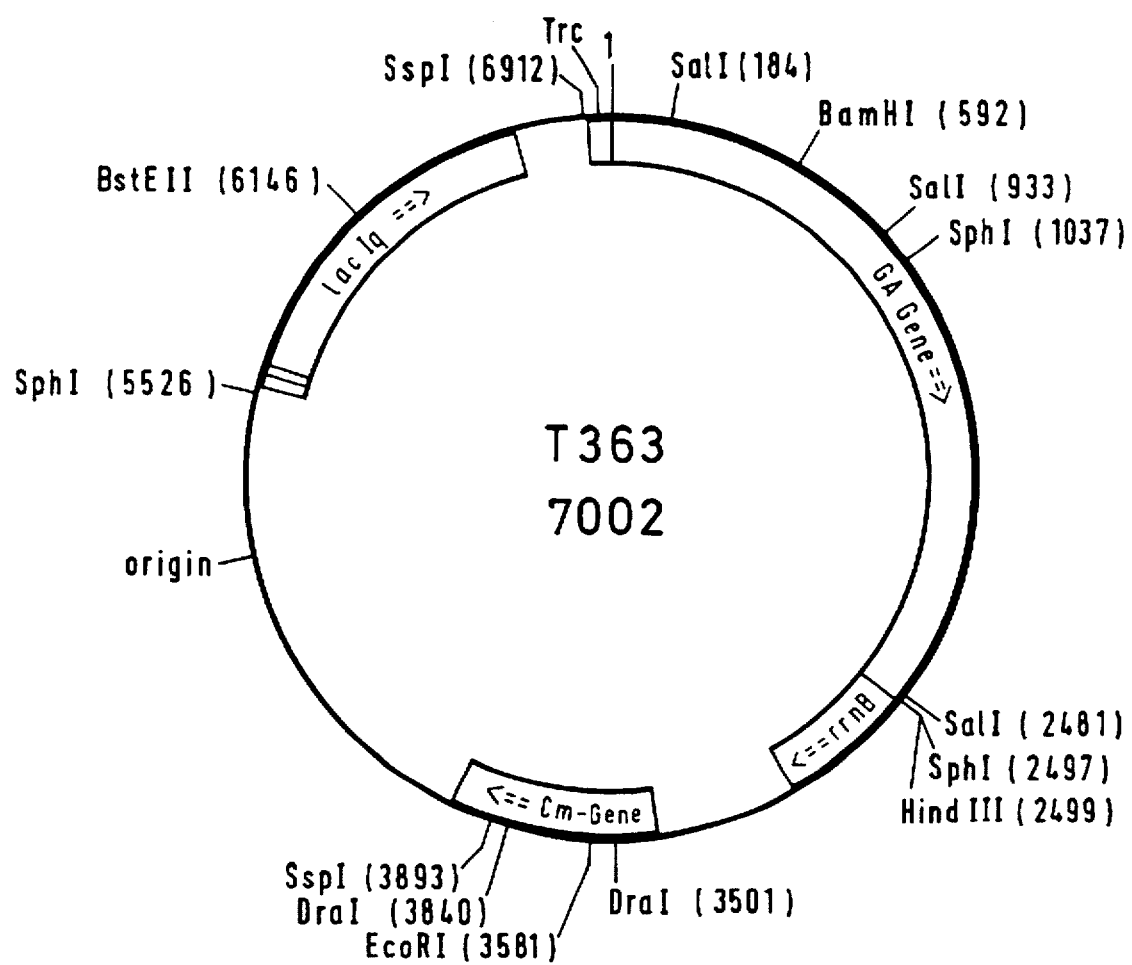

Analysis of the proteins formed by the E. coli strain W 3110 (T 396) in a 10 to 17.5% SDS polyacrylamide gel, after 2 days of cell growth under induction conditions, confirms, by comparison with the protein bands of the strain W 3110 (T 363; FIG. 4) which was cultured under the same conditions, that the CAT protein had decreased by more than 80%. Thus, while the yields of GA enzyme are very similar in the two strains, the ratio of the quantity of dissolved GA to that of total soluble protein following disruption of the cells is significantly improved, resulting, due to the lower quantity of foreign protein in relation to the GA, in the recovery of the glutarylamidase being markedly simplified.

EXAMPLE 2

Inactivation of the lac I$^q$ repressor gene (plasmid T 415)

Shaken culture experiments and fermentations had shown that the synthesis of GA was not, as expected, extensively switched off, prior to induction with IPTG, in any of the plasmids and E. coli strains used for forming GA. Furthermore, the induction rates described for the IPTG-dependent lac induction system did not conform with the values in the literature. In order to make the expression of GA completely independent of the use of an inducer such as IPTG, the reading frame encoding the lac I$^q$ repressor was destroyed. This results in an inactive repressor, thereby abolishing the block on the reading of the gene in the absence of inducer.

Figure 5:
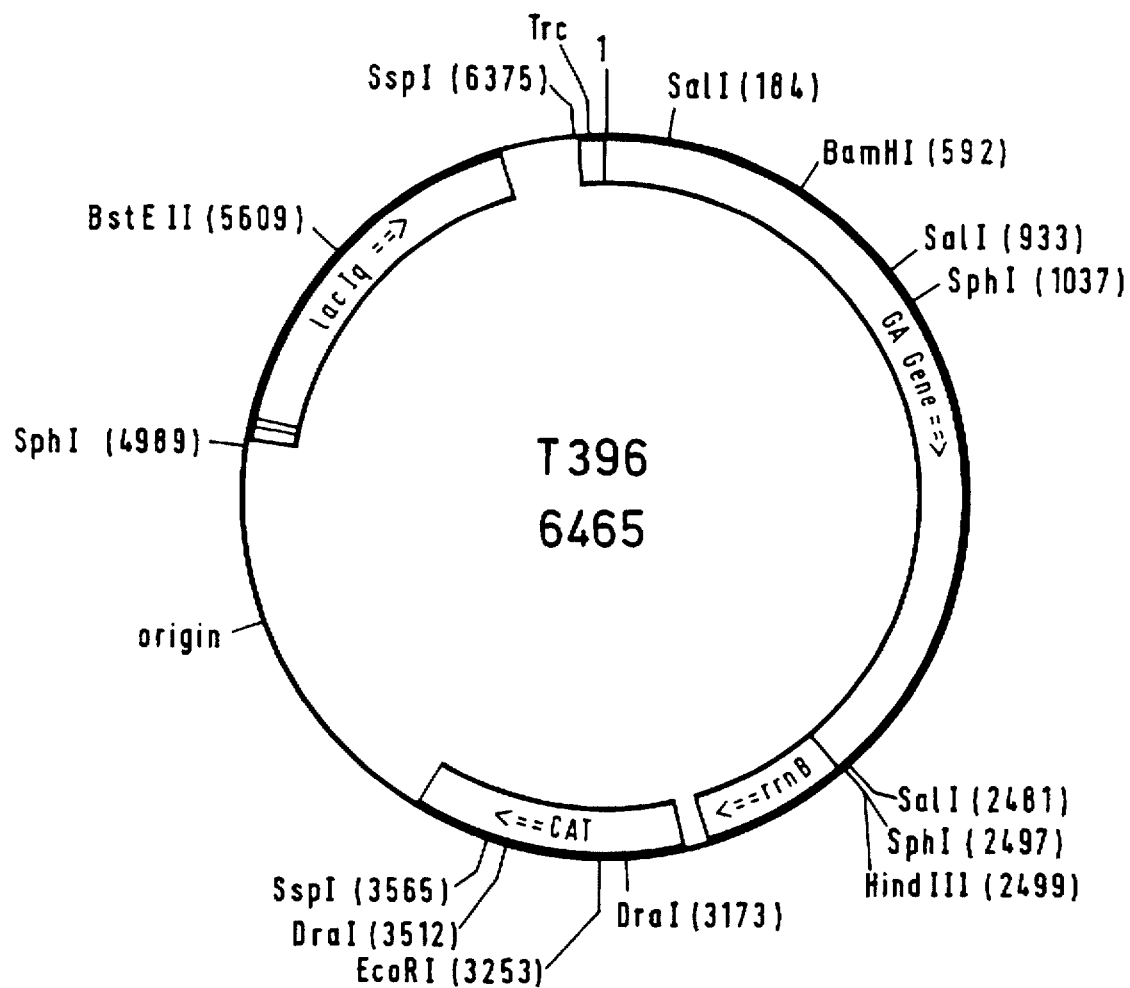
Figure 6:
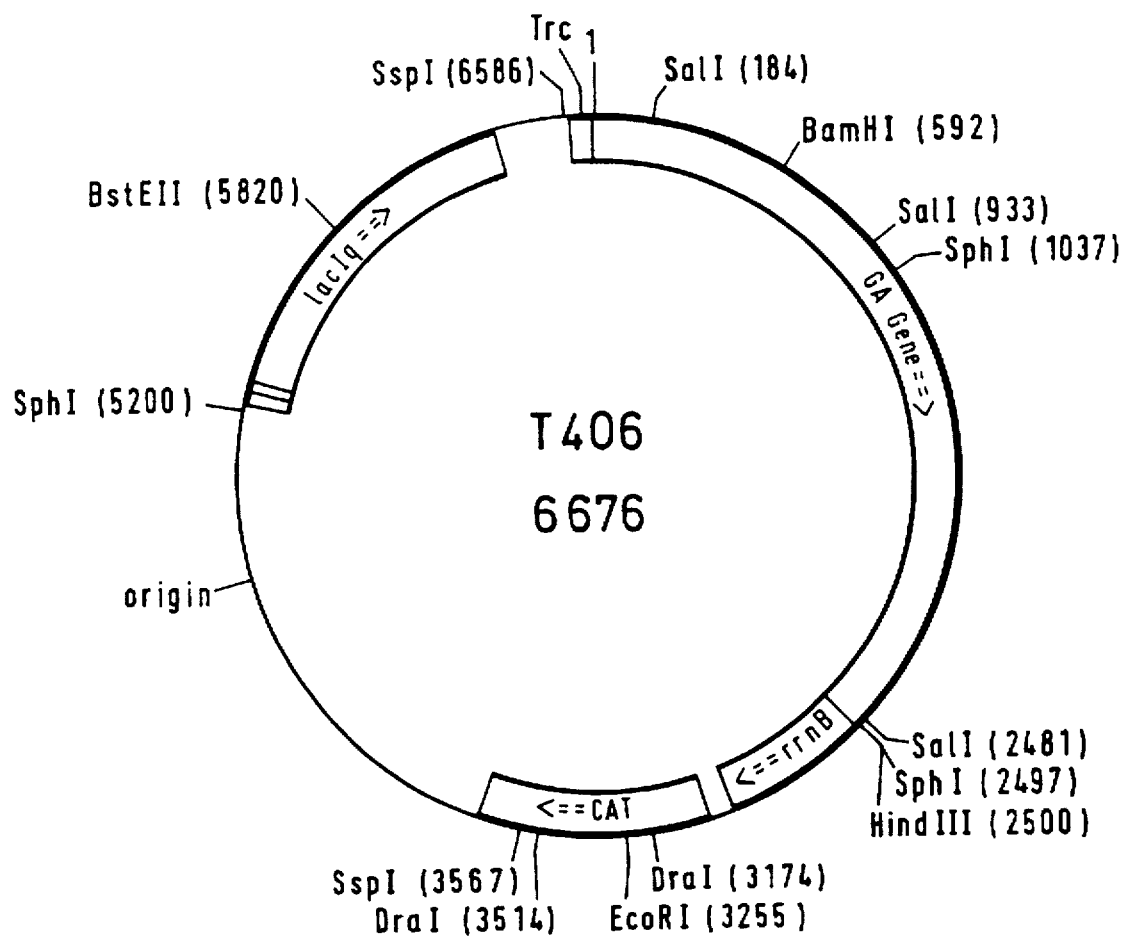

Isolated T 396 plasmid DNA (FIG. 5) was cut with the restriction enzymes EcoRI and HindIII and the approximately 750 bp fragment containing the region of the junction of the CAT gene with the β-lactamase promoter which resulted in reduced CAT gene expression was isolated by electroelution. This insert was then ligated together with the approximately 6000 bp EcoRI/HindIII fragment which had likewise been isolated from plasmid T 363. This results in the expression vector T 406 (FIG. 6). It has now been found, surprisingly, that vector T 406 is more stable than T 396 during fermentation.

Figure 7:
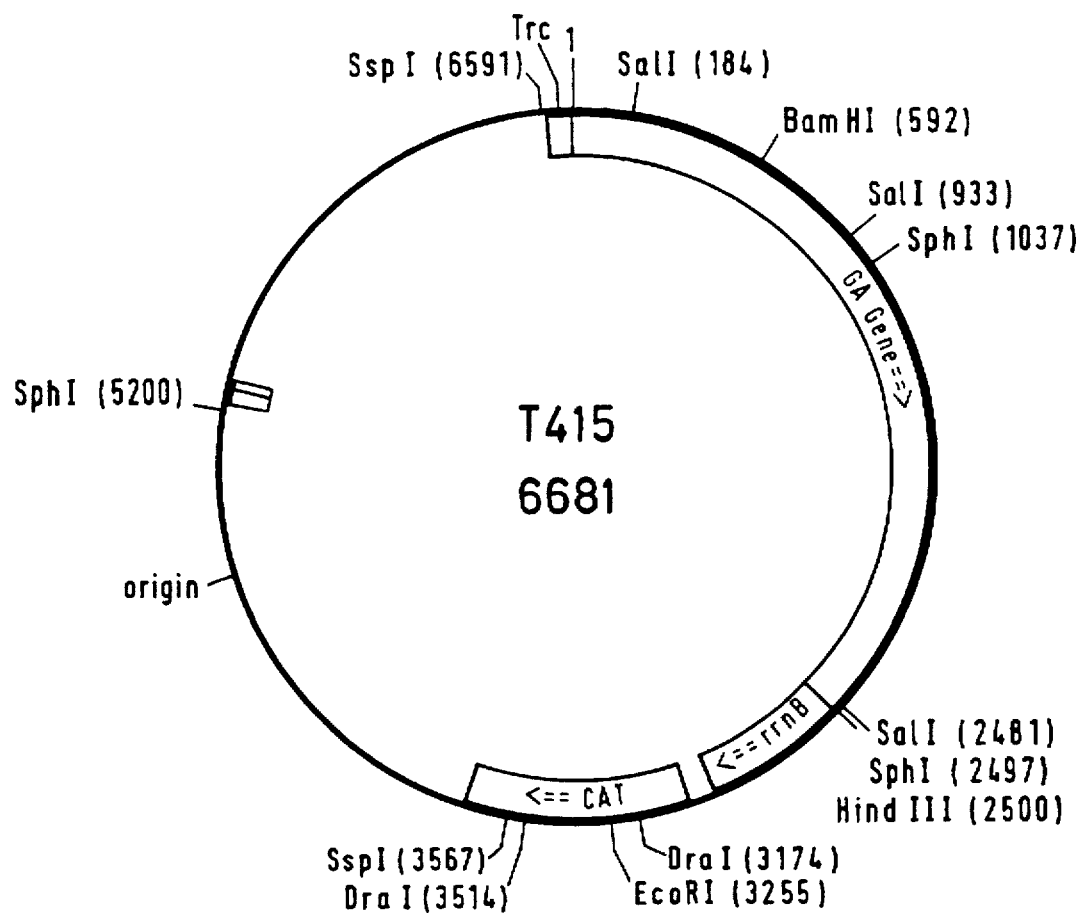

In order to inactivate the lac I$^q$ gene, isolated T 406 plasmid DNA was completely digested using the restriction enzyme BstEII. The unique cleavage site in the vector is located in the structural gene for the repressor. The protruding ends were filled in in the presence of dATP, dTTP, dGTP and dCTP using DNA polymerase, and the vector was religated in the presence of DNA ligase. This step causes the reading frame to shift by two base pairs so that no functional lac I$^q$ repressor can be formed. Plasmid T 415 results (FIG. 7). In shaken culture, recombinant E. coli W 3110 (T 415) clones exhibit an increase in the formation of GA from approximately 510 U/l after 2 days (T 363 with inducer) to 1590 U/l in the case of T 415, without inducer being added. In a control experiment, the yield is not improved by adding inducer to the T 415 system.

The recovery advantages which were demonstrated for *E. coli* strains harboring vector T 396 apply in equal measure to *E. coli* harboring plasmid T 415.

Since inactivating the lac I$^q$ repressor gene proved to be advantageous, it is also possible to consider using vectors which replicate in *E. coli* and which lack the lac I$^q$ gene from the start for making the constructs for constitutively expressing the GA. It also seems feasible to use *E. coli* strains for producing the GA in which, when the lac promoter/operator system is used, expression of the lac wild-type repressor, or of mutants thereof, is absent or takes place at low level.

EXAMPLE 3

Fermentation of *E. coli* T 415

In contrast to the *E. coli* clones T 347 and T 362/33 in accordance with EP-A-0 504 798, the glutarylamidase (GA) no longer needs to be induced by IPTG in the case of construct T 415. A description of an optimized fermentation is given below:

Culture Conditions:

With the exception of the parameters which were to be varied, all cultures were carried out under the following conditions:

Strains were preferably kept at −18° C. in YT/glycerol medium:

| | |
|---|---|
| Glycerol | 17.0% |
| Yeast extract | 0.7% |
| Bactotryptone | 0.4% |
| NaCl | 0.4% |
| Chloramphenicol | 12.5 µg/ml |

Agar plates of the same medium were set up from this suspension and incubated at 28° C. for 24 h, and the preculture (PC) was inoculated with a single colony.

| PC medium: | Bactotryptone | 2.0% |
|---|---|---|
| (NL 5295) | Bacto yeast extract | 1.0% |
| | NaCl | 0.5% |
| | Chloramphenicol | 12.5 µg/ml |
| | pH = 7.2 | |

100 ml volumes of this nutrient solution in 300 ml Erlenmeyer flasks were inoculated and then incubated at 28° C. and 220 rpm for from 16 to 24 h. The culture then had a $OD_{578nm}$ of 6.0 to 8.0.

The following main culture (MC) was inoculated with 5 to 10% (based on PC of $OD_{578nm}$=3.0) of this PC:

MC: NL 5292+1 ml of Desmophen

| | |
|---|---|
| 20.0 g/l | Yeast extract (Oxoid) |
| 1.2 g/l | $NaH_2PO_4 \times H_2O$ |
| 8.5 g/l | $Na_2HPO_4 \times 2H_2O$ |
| 1.0 g/l | KCl |
| 2.0 g/l | $MgSO_4 \times 7H_2O$ (autoclaved separately) |
| 0.25 g/l | Citric acid |
| 5.0 g/l | $NH_4Cl$ |
| 4.0 g/l | SLA 5029 |
| 0.005 g/l | Thiamine → sterilized by filtration (5 mg/10 ml → 0.5/50 ml of NL) |
| pH = 6.5 | |

Fermentation conditions: temp.: 28° C.
vol.: 3.5 l
vvm: 0.75
rpm: 500 (r=7 cm)
pH: 7.0±0.2 (kept constant using 25% $NH_4OH$)

| | |
|---|---|
| Fed-batch: Glycerol solution: | 525 g of glycerol (99%)/l of MC medium (without $NH_4Cl$) |
| Feeding rate: | 3.4 ml/l/h with continuous addition (max. glycerol conc. in the fermenter: 0.2%) |
| Feeding begun: | during the 5th hour of fermentation |
| Duration of feeding: | 40 to 70 h |
| $pO_2$: | kept constant at approximately 40% |

EXAMPLE 4 DEMONSTRATION THAT EXPRESSION OF THE GA IS INDEPENDENT OF IPTG

For this purpose, clone T 415 was cultured in a fermenter under the above conditions and two Erlenmeyer flasks were in each case filled with 50 ml of culture solution at different time points. One flask was induced with 1 mM IPTG while the other was not. The following GA volume activities were measured:

| Time of | GA (U/l)* | |
|---|---|---|
| removal | +IPTG | without IPTG |
| 23 h | 2700 | 2800 |
| 31 h | 2600 | 2600 |
| 47 h | 4400 | 4500 |

*24 h after filling the flasks

The experiment clearly demonstrates that IPTG is no longer required for inducing GA.

EXAMPLE 5 FERMENTATION OF *E. coli* T 415

8200 U of GA/l of culture solution (CS) were achieved after 73 hours of fermentation under the above described conditions. The specific activity was approximately 70 U/g of moist weight. The biomass yield was approximately 120 g of moist weight/l.

EXAMPLE 6 FERMENTATION USING A MODIFIED MC MEDIUM

Doubling the concentration of yeast extract in the MC medium from 20 to 40 g/l resulted in an enhancement of the rate of growth and in an increase of the biomass yield to approximately 140 g/l. The GA volume activity rose to 9600 U/l of CS after 73 hours. 8000 U/l were achieved after only 48 hours, denoting a shortening of the fermentation period by one day.

EXAMPLE 7 FERMENTATION USING MODIFIED FED-BATCH FEEDING

Elimination of the IPTG-dependent regulation of GA expression rendered it possible not only (Example 6) to examine the possibility of successfully amplifying the MC medium, but also to vary the rate of feeding glycerol, which had previously been limiting owing to the formation of acetate. If, for example, the feeding rate was increased, from the 5th to the 8th hour of fermentation, continuously from 3.4 ml/l/h to 6.6 ml/l/h, and was then held constant until the end of the fermentation, this led to an extension of the rapid, optimum phase of growth, as a result of which the clone formed the enzyme at a constant, elevated rate of synthesis until the 73rd hour, and, in the end, up to 18,800 U were produced per liter of CS. Taking into account the specific activity of the GA of 7 U/mg of protein, more than 2.5 g of enzyme were thus formed per liter of CS. The biomass yield was approximately 200 g/l of CS. Only a small quantity of acetate, of at most 3–4 g/l, was still formed as an intermediate.

We claim:

1. A process for preparing glutarylamidase (GA) from bacteria, comprising:
   (a) inoculating a culture medium with a recombinant bacteria that constitutively expresses a GA gene from an expression vector;
   (b) incubating said culture medium under conditions that permit synthesis of GA; and optionally,
   (c) recovering GA from said culture medium.

2. The process as claimed in claim 1, wherein said expression vector further comprises a promoter for constitutively expressing said GA gene, said promoter being a trc promoter, or a trc-equivalent promoter, without any repressor or with a non-functional repressor.

3. The process as claimed in claim 2, wherein said expression vector further comprises a selection gene which encodes a protein which remains in said bacteria and is not periplasmic.

4. The process as claimed in claim 3, wherein the expression of said protein encoded by said selection gene is weak.

5. The process as claimed in claim 4, wherein said selection gene encodes chloramphenicol acetyltransferase (CAT).

6. The process as claimed in claim 5, further comprising feeding a carbon source to a fermenting bacteria culture at a feeding rate, wherein the feeding rate is increased during a main culture.

7. The process as claimed in claim 6, wherein said feeding rate is increased during a logarithmic phase of growth.

8. The process as claimed in claim 7, wherein said carbon source is glycerol.

9. The process as claimed in claim 8, wherein approximately 10–50 g/l of a complex nitrogen source are used in the fermentation of the bacteria.

* * * * *